United States Patent [19]

Martin et al.

[11] 4,354,028
[45] Oct. 12, 1982

[54] PIPERAZINE DERIVATIVES

[75] Inventors: John Martin, Carmel, Ind.; George A. Doorakian, Bedford; Lawrence G. Duquette, Maynard, both of Mass.

[73] Assignee: The Dow Chemical Company, Midland, Mich.

[21] Appl. No.: 252,635

[22] Filed: Apr. 9, 1981

Related U.S. Application Data

[63] Continuation-in-part of Ser. No. 114,022, Jan. 21, 1980, abandoned.

[51] Int. Cl.³ ............................................. C07D 405/04
[52] U.S. Cl. ....................................... 544/374; 252/73; 252/190; 252/392; 252/394; 544/398; 544/401
[58] Field of Search ......................... 544/374, 398, 401

[56] References Cited

U.S. PATENT DOCUMENTS 3,092,637  6/1963  Brown ............................... 260/326.5
3,920,746  11/1975  Leimgruber et al. ............... 564/405
4,170,653  10/1979  Ferland et al. ....................... 544/401

OTHER PUBLICATIONS

Gloede, et al., "Zeitschrift für Chemi", vol. 9, No. 6, 1969, pp. 201–213.
Meerwein, "Angew Chem.," vol. 71, 1959, p. 530.

Primary Examiner—Donald G. Daus
Assistant Examiner—James H. Turnipseed
Attorney, Agent, or Firm—Douglas N. Deline

[57] ABSTRACT

Novel amide acetals of the formula

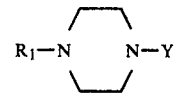

wherein $R_1$ is hydrogen, methyl or Y and Y is the remnant of a hydroxyl-containing compound are claimed. The compounds are useful as water scavengers in fluid compositions.

4 Claims, No Drawings

PIPERAZINE DERIVATIVES

CROSS REFERENCE TO RELATED APPLICATION

This is a continuation-in-part of copending application Ser. No. 114,022, filed Jan. 21, 1980, now abandoned.

BACKGROUND OF THE INVENTION

The invention relates to novel compounds that are useful additives to functional fluids. By the term "functional fluids" is meant fluids commonly adapted for the transfer of mechanical or thermal energy including hydraulic fluids, for example, fluids employed in braking systems of automobiles, trucks and military vehicles, power steering systems and actuating devices and controls for automobiles, airplanes, ships; shock absorbing devices, jacks and door closures, etc. Also included are heat absorbing and transporting fluids for use in transformers and other electrical or mechanical devices. In particular the fluids are those designed to remain essentially anhydrous or if contaminated by small quantities of water, as for example, by absorption from contact with the atmosphere, the fluids should remain substantially unaffected in their desired qualities.

It is customary, in order to provide a fluid suitable for use as a functional fluid, to incorporate into the formulation of such a fluid a water-scavenging agent capable of reacting with small amounts of water so as to render the fluid unaffected by contamination with water.

A further desirable additive for functional fluid compositions are corrosion inhibitors, in particular compounds useful in reacting with acids such that the fluid retains a neutral or slightly alkaline pH. A functional fluid so designed has been found to be less likely to promote corrosion and premature failure of metal parts in contact with the fluid.

Amide acetals were first reported by Meerwein, *Angew. Chem.*, 71, 530 (1959) who taught that the compounds were quite versatile, highly reactive intermediates.

In U.S. Pat. No. 3,092,637, acetals and ketals of N,N-disubstituted carboxyamides of the formula

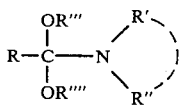

wherein R', R'', R''' and R'''' are specified hydrocarbyl radicals and R is hydrogen or hydrocarbyl, are disclosed. Also taught is a process for making the compounds by reacting an alkali metal or alkaline earth metal salt of an alcohol or phenol with a 1,1-dihalosubstituted tertiary amine.

It is known that amide acetals exchange oxygen-containing functionalities upon heating with higher boiling alcohols and phenols. The compounds also condense without a catalyst with compounds containing a labile methyl or methylene to form corresponding methylene amine compounds.

SUMMARY OF THE INVENTION

Amide acetals of the present invention may be represented by the formula

where $R_1$ is hydrogen, $C_{1-4}$ alkyl or hydroxyalkyl, or the radical Y; and Y independently each occurrence is selected from:

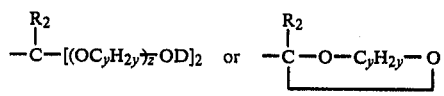

where $R_2$ is hydrogen or methyl, D is hydrogen or $C_{1-4}$ alkyl, y independently each occurrence is 2, 3 or 4 and z is 0, 1, 2, 3 or 4.

Preferably, the hydrolysis products formed by the reaction of water with the above compounds, e.g., $H\text{-}(OC_yH_{2y}\text{-})_{2}OD$, have boiling points above about 155° C. Most preferred compounds are 1-(dioxolan-2-yl)piperazines and 1-methyl-4-(dioxolan-2-yl)piperazines.

These piperazine containing amide acetals are useful in a variety of applications including being useful water-scavenging additives for functional fluids, especially hydraulic fluids. Furthermore, the presence of the compounds in fluid formulations has also been found to inhibit corrosion due to acids.

DETAILED DESCRIPTION OF THE INVENTION

The compounds of the invention are amide acetals containing in addition piperazine or N-substituted piperazine functionality. They are easily formed by contacting amide acetals prepared according to the method of Meerwein, supra, and optionally further transacetylated derivatives thereof with piperazine or N-alkyl or N-hydroxyalkyl-substituted piperazine compounds. Preferred reactants are 1-alkylpiperazines having from 1 to 4 carbons in the alkyl substituent. The reaction is illustrated in the following schematic drawing.

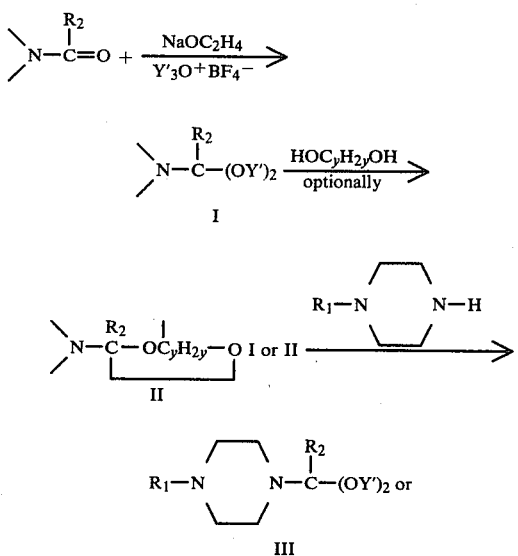

-continued

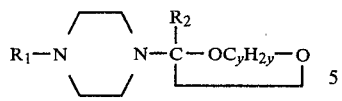

where OY' is $-\!(OC_yH_{2y})_z\!-\!OD$ and y, z and D are as previously defined.

The initial reaction of a N,N-dihydrocarbon-substituted carboxamide with an oxonium fluoroborate in the presence of an alkali metal alkoxide was previously disclosed by Meerwein, supra. Other methods may also be used to produce the intermediate amide acetal I, for example, the procedure disclosed in U.S. Pat. No. 3,092,637.

The optional transacetylation reaction with an alkylene glycol is also a known reaction and easily accomplished by contacting an alkylene glycol and the intermediate amide acetal at elevated temperatures. The product is the corresponding cyclic ether II. It is also possible to produce the non-cyclic amide acetal, I, by transacetylation of simpler alkyl substituted amide acetals with hydroxyl compounds of the formula HOY' in the same manner. Preparation of such compounds is also known having been described in Gloede et al., *Zeitschrift fur Chemie*, 9 (6), 201–213 (1969).

The compounds of the instant invention are easily prepared by contacting (I) or (II) with the previously described piperazine compounds. The reaction is easily accomplished by contacting the reactants with mixing, optionally accompanied by heating according to the known techniques of transamination reactions. The products may be recovered by ordinary laboratory techniques.

The compounds may be easily formulated with other unreactive components to provide improved hydraulic or other functional fluids. Preferred components are the well-known alkylene and polyalkylene glycols and monoalkyl ethers thereof. The compounds of the invention effectively act as both water-scavengers and acid acceptors. Fluids containing the invented compounds are therefore protected from the deleterious effects of both water and acid contamination of the fluid.

Upon contacting with water the invented compounds are easily hydrolyzed by reaction of the acetal functionality. The reaction products are the corresponding amide and one or more hydroxyl compounds of the formula $HO(C_yH_{2y})_zOD$. In the preferred embodiment the hydroxyl compounds formed have normal boiling points, i.e., boiling points at atmospheric pressure, above about 155° C. Such hydrolysis products will not degrade the wet boiling point of a functional fluid composition below the minimum wet equilibrium reflux boiling point of the DOT-4 standard specified in Federal Motor Vehicle Safety Standard #116, 49 CFR §571.116.

Preferably the compounds are present in the functional fluid from about 0.1 to about 20 percent by weight. Most preferably from 1 to 10 percent by weight.

SPECIFIC EMBODIMENTS

The following examples are included as illustrative of the present invention and are not to be construed as limiting.

EXAMPLE 1

1-methyl-4-(diethoxymethyl)piperazine

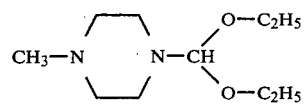

A quantity of N,N-dimethylaminodiethoxymethane,

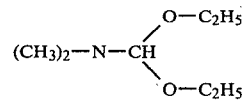

(4.41 g, 0.03 mole), prepared by the previously cited method of Meerwein was combined with N-methylpiperazine (3.0 g, 0.03 mole), in a glass reactor under an inert atmosphere of nitrogen. Heating was commenced and the mixture maintained at about 183° C. for about two hours. Dimethylamine formed during the reaction was removed with a dry nitrogen stream. A yellow liquid was obtained which on vacuum distillation gave 4.2 g, 97 percent yield of a clear product having a boiling point of 225° C. Identification by NMR spectrum proved the structure to be 1-methyl-4-(diethyoxymethyl)piperazine.

EXAMPLE 2

1-methyl-4-(dioxolan-2-yl)piperazine

The amide acetal produced in Example 1 (3.03 g, 0.015 mole) was combined while stirring with ethylene glycol (0.93 g, 0.015 mole) in a glass flask at ambient temperature under nitrogen. The reaction was continued with stirring for 18 hours. The by-product ethanol formed during the reaction was removed by vacuum and the reaction continued for an additional 18 hours with stirring under vacuum. The resulting product was found to have a boiling point of about 220° C., and identified as the desired product by NMR spectroscopy.

EXAMPLE 3

Evaluation as Water Scavenger

A sample of water was rapidly mixed with the compound prepared in Example 2 above in a stoichiometric ratio of 1.3:1. The reaction at room temperature was observed by NMR spectroscopy. Approximately 20 percent of the amide acetal reacted in the first five minutes. Essentially complete reaction occurred in 24 hours. The primary reaction products were found to be ethylene glycol and 1-methyl-4-formyl-piperazine having a boiling point of about 220° C.

EXAMPLE 4

Corrosion Inhibition

The ability of the above hydrolysis product 1-methyl-4-formylpiperazine to react with acids was illustrated by essentially instantaneous reaction of the latter with HCl at room temperature. Furthermore, a sample of 1-methyl-4-formylpiperazine when added in equivalent amount to solutions of HCl in water and ethylene glycol, respectively, rapidly produced changes in pH from initial values of less than 1 to values of 7 and 5, respectively.

EXAMPLE 5

A sample hydraulic fluid was prepared having the following formulation:

| Component | Wt. % |
| --- | --- |
| lower alkyl ethers of polyethylene glycol | 69 |
| polyethylene glycol | 6 |
| mixed polyethylene and polypropylene glycols | 25 |
| inhibitors | <1.0 |

This formulation meeting U.S. Gov. DOT-3 specifications was then tested according to F.M.V.S.S., #116, 49 CFR §571.116 with various percentages of 1-methyl-4-(dioxolan-2-yl)piperazine added. The results are contained in Table I. It may be seen that the invented compounds may be used to improve the water compatibility of the fluid as indicated by the improved wet boiling point.

TABLE I

|  | U.S. Gov. DOT-3 Specif. | % by Vol. 1-methyl-4-(dioxolan-2-yl)piperazine | | | | U.S. Gov. DOT-4 Specif. |
| --- | --- | --- | --- | --- | --- | --- |
|  |  | 0% | 3% | 5% | 10% |  |
| Dry b.p. (°C.) minimum | 205 | 469 | 476 | 475 | 465 | 230 |
| Wet b.p. (°C.) minimum | 140 | 296 | 304 | 309 | 319 | 155 |
| Viscosity (cSt/−40° F.): |  |  |  |  |  |  |
| Dry formulation | 1500[1] | 907 | 981 | 1060 | 1254 | 1800[1] |
| Wet formulation |  | 1222 | 1310 | 1428 | 1484 |  |
| Rubber Swell (IRHD/inches):[2] |  |  |  |  |  |  |
| Dry formulation |  | 12.7/.042 | 13.0/.044 | 12.0/.045 | 16.8/.057 |  |
| Wet formulation |  | 13.0/.034 | 14.0/.032 | 14.5/.032 | 13.0/.034 |  |
| pH | 7–11.5 | 10.2 | 9.9 | 9.9 | 10.1 | 7–11.5 |

[1]Maximum cSt
[2]IRHD - International Rubber Hardness Degree (the hardness of the brake cup cannot decrease by more than 15 IRHD at 248° F. for 3 days).
Inches - The base diameter of the brake cup cannot increase by more than 0.055 inches.

What is claimed is:

1. A compound represented by the formula

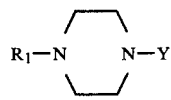

where $R_1$ is hydrogen, $C_{1-4}$ alkyl or hydroxyalkyl, or the radical Y; and Y independently each occurrence is selected from:

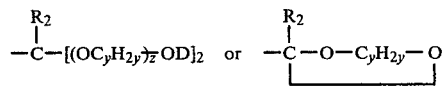

where $R_2$ is hydrogen or methyl, D is hydrogen or $C_{1-4}$ alkyl, y independently each occurrence is 2, 3 or 4 and z is 0, 1, 2, 3 or 4.

2. A compound of claim 1 wherein $R_1$ is hydrogen or methyl.

3. A compound of claim 1 wherein Y is

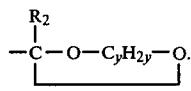

4. A compound of claim 3 which is 1-methyl-4-(dioxolan-2-yl)piperazine.

* * * * *